United States Patent
Cooney et al.

(10) Patent No.: US 11,767,549 B2
(45) Date of Patent: Sep. 26, 2023

(54) INTEGRATED SAMPLE PROCESSING SYSTEM

(71) Applicant: AKONNI BIOSYSTEMS, INC., Frederick, MD (US)

(72) Inventors: Christopher G. Cooney, Ellicott City, MD (US); Rebecca Holmberg, Rockville, MD (US); Phillip Belgrader, Livermore, CA (US); Peter Qiang Qu, New Market, MD (US)

(73) Assignee: AKONNI BIOSYSTEMS, INC., Frederick, MD (US)

( * ) Notice: Subject to any disclaimer, the term of this patent is extended or adjusted under 35 U.S.C. 154(b) by 161 days.

(21) Appl. No.: 17/137,807

(22) Filed: Dec. 30, 2020

(65) Prior Publication Data

US 2021/0230668 A1 Jul. 29, 2021

Related U.S. Application Data

(60) Continuation of application No. 16/158,129, filed on Oct. 11, 2018, now abandoned, which is a
(Continued)

(51) Int. Cl.
*C12Q 1/68* (2018.01)
*C12Q 1/6806* (2018.01)
(Continued)

(52) U.S. Cl.
CPC .......... *C12Q 1/6806* (2013.01); *B01L 3/5082* (2013.01); *B01L 3/52* (2013.01);
(Continued)

(58) Field of Classification Search
USPC .......... 435/6.1, 6.11, 7.1, 91.1, 283.1, 287.1, 435/287.2; 436/94; 536/23.1; 530/300,
(Continued)

(56) References Cited

U.S. PATENT DOCUMENTS

2004/0259093 A1* 12/2004 Sakurai .............. C12N 15/1006
536/25.4
2011/0189759 A1* 8/2011 Himmelrich .......... C12N 1/066
435/259

FOREIGN PATENT DOCUMENTS

DE 3627132 * 8/1986
WO 2009092662 A1 * 7/2009 ............. C12N 1/066

OTHER PUBLICATIONS

Aldous et al.,Comparison of Six Methods of Extracting Mycobacterium tuberculosis DNA from Processed Sputum forTesting by Quantitative Real-Time PCR. Journal of Clinical Microbiology, 43, 2471-2473, 2005.*

* cited by examiner

*Primary Examiner* — Frank W Lu
(74) *Attorney, Agent, or Firm* — Michael Ye; Rimon Law

(57) ABSTRACT

An integrated sample purification system includes a housing, a sample container rack, a filter holder, and a cylindrical magnet. The sample container rack and the filter device holder are disposed in the housing. The sample container rack is configured to hold one or more sample containers, the filter device holder is configured to hold one or more filter devices. The cylindrical magnet is adjacent to and external to the sample container rack, and is rotated about a central, longitudinal axis of the magnet by an electric motor disposed in the housing to lyse cells. Molecules of interest in the lysed cells are purified using filters that bind specifically to the molecules of interest. The system is readily amenable to automation and rapid purification and analysis of molecules of interest, such as nucleic acids and proteins.

10 Claims, 7 Drawing Sheets

Related U.S. Application Data continuation of application No. 14/955,681, filed on Dec. 1, 2015, now Pat. No. 10,125,388, which is a continuation-in-part of application No. 14/294,683, filed on Jun. 3, 2014, now Pat. No. 9,493,815, which is a continuation-in-part of application No. 14/011,267, filed on Aug. 27, 2013, now Pat. No. 9,428,746, which is a continuation-in-part of application No. 13/765,399, filed on Feb. 12, 2013, now Pat. No. 9,217,174, which is a continuation of application No. 12/886,144, filed on Sep. 20, 2010, now Pat. No. 8,399,190, said application No. 14/955,681 is a continuation-in-part of application No. 14/294,683, filed on Jun. 3, 2014, now Pat. No. 9,493,815, which is a continuation of application No. 13/446,291, filed on Apr. 13, 2012, now Pat. No. 8,828,912, which is a continuation-in-part of application No. 12/886,201, filed on Sep. 20, 2010, now Pat. No. 8,623,789, said application No. 14/955,681 is a continuation-in-part of application No. 14/011,267, filed on Aug. 27, 2013, now Pat. No. 9,428,746, which is a continuation-in-part of application No. 13/682,551, filed on Nov. 20, 2012, now Pat. No. 8,574,923, which is a division of application No. 12/213,942, filed on Jun. 26, 2008, now abandoned, which is a continuation-in-part of application No. 11/933,113, filed on Oct. 31, 2007, now Pat. No. 7,759,112.

(60) Provisional application No. 61/272,396, filed on Sep. 21, 2009, provisional application No. 61/272,397, filed on Sep. 21, 2009, provisional application No. 61/475,107, filed on Apr. 13, 2011, provisional application No. 61/697,116, filed on Sep. 5, 2012, provisional application No. 61/693,963, filed on Aug. 28, 2012.

(51) Int. Cl.
*G01N 35/10* (2006.01)
*B01L 3/00* (2006.01)
*B01L 9/06* (2006.01)
*G01N 35/00* (2006.01)
*C12N 1/06* (2006.01)
*C12N 13/00* (2006.01)
*C12Q 1/689* (2018.01)

(52) U.S. Cl.
CPC ................ *B01L 9/06* (2013.01); *C12N 1/066* (2013.01); *C12N 13/00* (2013.01); *C12Q 1/689* (2013.01); *G01N 35/0099* (2013.01); *G01N 35/1002* (2013.01); *B01L 2300/0609* (2013.01); *B01L 2300/0832* (2013.01)

(58) Field of Classification Search
USPC ....................................................... 530/350
See application file for complete search history.

10

PLACING A SAMPLE TUBE CONTAINING A LIQUID SAMPLE SUSPENSION, A MAGNETIC STIRRER AND CELL LYSIS BEADS ON A SAMPLE RACK IN THE PROXIMITY OF A MAGNET — 11

HOMOGENIZING THE SAMPLE SUSPENSION BY ROTATING THE MAGNET AT A SPEED SUFFICIENT TO LYSE CELLS IN THE SAMPLE SUSPENSION IN THE PRESENCE OF THE MAGNETIC STIRRER AND CELL LYSIS BEADS — 13

FLOWING THE HOMOGENIZED SAMPLE SUSPENSION THROUGH A FILTER MATRIX SO THAT THE MOLECULES OF INTEREST BIND TO THE FILTER MATRIX — 15

WASHING THE FILTER MATRIX — 17

ELUTING THE MOLECULES OF INTEREST FROM THE FILTER MATRIX — 19

*FIG. 1*

INTEGRATED SAMPLE PROCESSING SYSTEM

The instant application is a continuation application of U.S. application Ser. No. 16/158,129, filed on Oct. 11, 2018, which is a continuation of U.S. application Ser. No. 14/955,681, filed Dec. 1, 2015, now U.S. Pat. No. 10,125,388 which is a continuation-in-part application of U.S. application Ser. No. 13/765,399, filed on Feb. 12, 2013, now U.S. Pat. No. 9,217,174, which is a continuation application of U.S. application Ser. No. 12/886,144, filed on Sep. 20, 2010, now U.S. Pat. No. 8,399,190, which claims the priority of U.S. Provisional Application No. 61/272,396, filed on Sep. 21, 2009.

U.S. application Ser. No. 14/955,681, now U.S. Pat. No. 10,125,388, is also a continuation-in-part application of U.S. application Ser. No. 14/294,683, filed on Jun. 3, 2014, now U.S. Pat. No. 9,493,815, which is a continuation of U.S. application Ser. No. 13/446,291, filed on Apr. 13, 2012, now U.S. Pat. No. 8,828,912, which is a continuation-in-part of U.S. application Ser. No. 12/886,201, filed on Sep. 20, 2010, now U.S. Pat. No. 8,623,789, which claims priority to U.S. Provisional Application No. 61/272,397, filed on Sep. 21, 2009, and U.S. application Ser. No. 13/446,291, filed Apr. 13, 2012, also claims priority to U.S. Provisional Application No. 61/475,107, filed on Apr. 13, 2011.

U.S. application Ser. No. 14/955,681, now U.S. Pat. No. 10,125,388, is also a continuation-in-part of U.S. application Ser. No. 14/011,267, filed on Aug. 27.2013, now a U.S. Pat. No. 9,428,746, which is a continuation-in-part application of U.S. application Ser. No. 13/682,551, filed on Nov. 20, 2012, now U.S. Pat. No. 8,574,923, which is a divisional application of U.S. application Ser. No. 12/213,942, filed on Jun. 26, 2008, now abandoned, which is a continuation-in-part application of U.S. application Ser. No. 11/933,113, filed on Oct. 31, 2007, now U.S. Pat. No. 7,759,112. U.S. application Ser. No. 14/011,267 also claims priority of U.S. Provisional Application No. 61/697,116, filed on Sep. 5, 2012 and U.S. Provisional Application No. 61/693,963, filed on Aug. 28, 2012.

U.S. application Ser. No. 14/955,681, now U.S. Pat. No. 10,125,388, is also a continuation-in-part application of U.S. application Ser. No. 13/314,734, filed on Dec. 8, 2011, now U.S. Pat. No. 10,300,482, which claims the priority of U.S. Provisional Application No. 61/421,414, filed on Dec. 9, 2010.

The entirety of all of the aforementioned applications is incorporated herein by reference.

FIELD

The present invention relates generally to an integrated sample processing system for isolating and/or purifying molecules of interest, such as nucleic acids and proteins, especially from difficult sample matrices and/or difficult-to-disrupt organisms, as well as methods amenable to automation for isolating and/or purifying nucleic acids from a sample using magnetically-induced vortexing in combination with solid monolith filters.

BACKGROUND

Molecular testing is emerging as a gold standard for some diagnostic tests due to their speed, sensitivity and specificity. Laboratory Developed Tests (LDTs) "are now one of the fastest growing segments in the in vitro diagnostic (IVD) market. Sample preparation is critical to the validity of the test, but frequently presents a bottleneck for clinical molecular biology workflows and diagnostic tests. While there are many molecular detection modalities, there are only a handful of automated sample preparation workflow strategies. Existing instruments that are built around these sample preparation strategies and chemistries range in cost from $17-$150 k, and yet they still do not provide an integrated method for processing difficult sample matrices such as raw sputum and/or difficult-to-disrupt organisms such as gram-positive bacteria and the acid fast bacilli (i.e., *Mycobacterium*).

Acid fast bacilli, including *Mycobacterium* strains are typically isolated from sputum of infected patients. They are known as "acid-fast bacilli" because of their lipid-rich cell envelope, which is relatively impermeable to various basic dyes unless the dyes are combined with phenol. Sputum is thick, viscous and difficult to process. Most sputum specimens for analysis contain various amounts of organic debris and a variety of contaminating, normal, or transient bacterial flora. Chemical decontamination/processing is typically used to reduce the viscosity and kill the contaminants while allowing recovery of the mycobacteria. Because of their unique cell envelope containing mycolic acids and a high lipid content, however, the cells are hydrophobic and tend to clump together. This renders them impermeable to the usual stains, such as the Gram stain. Two types of acid-fast stains are generally used, carbol fuchsin and fluorochromes, such as auramine or auramine-rhodamine. Once stained, the cells resist decolorization with acidified organic solvents, and are therefore called "acid-fast". However, they retain fuchsine or auramine staining after successive or simultaneous treatment with acid and alcohol.

The sensitivity of acid-fast smear microscopy for *Mycobacterium* species is poor. The sensitivity of microscopy is influenced by numerous factors, such as the prevalence and severity of disease, the type of specimen, the quality of specimen collection, the number of *Mycobacterium* cells present in the specimen, the method of processing (direct or concentrated), the method of centrifugation, the staining technique, and the quality of the examination. It is recommended that a negative result should only be reported following the examination of at least 100 (in low-income countries) and preferably 300 (in industrialized countries) microscopic immersion view fields (or equivalent fluorescent view fields). Therefore, when microscopy is performed correctly, it can be time-consuming and laborious.

*Mycobacterium* strains are slow-growing bacilli, with a usual generation time of 12 to 18 hours. Colonies usually become visible only after a 1-week to 8-week incubation time. Samples which contain a low concentration of *Mycobacterium* cells further necessitate several subcultures. *Mycobacterium* cultures on specific media can allow for the identification of the particular *Mycobacterium* species contained in the biological sample. However, this is time-consuming, especially for those patients who are only at the beginning of the infection process.

Nucleic acid hybridization tests have been developed to detect strains of *Mycobacterium* in a biological sample. The first tests utilized direct probe hybridization. However, the concentration in *Mycobacterium* cells contained in a sample collected from a patient is usually too low to give a positive hybridization signal. Tests utilizing PCR amplification have therefore been developed. For example, the Gen-Probe® kit commercialized as "Amplified™ *Mycobacterium tuberculosis* direct test" kit, or MTD test kit, (Gen-Probe Inc., San Diego, Calif. 92121, USA) utilizes the amplification of MtbC-specific rRNA (Transcription-Mediated Amplification), followed by amplicon detection in accordance with the Gen-Probe HPA method (Hybridization Protection Assay).

In view of the above-described limitations, there is a need for simple and efficient systems integrating sample homogenization, lysis of difficult-to-disrupt microorganisms, and polynucleotide purification to meet the needs of both clinical laboratories and users alike.

SUMMARY

In one aspect, the present application provides an integrated sample purification system comprising housing, a sample container rack, a filter tip rack, and a cylindrical magnet. The sample container rack and the filter tip rack are disposed in the housing. The sample container rack is configured to hold one or more sample containers, the filter tip rack is configured to hold one or more filter tips. The cylindrical magnet is adjacent to and external to the sample container rack, and is rotatably driven about a central, longitudinal axis of the magnet by an electric motor disposed in the housing.

In some embodiments, the housing comprises one or more reagent racks containing one or more reagents.

In some embodiments, the system comprises a plurality of the sample containers, a plurality of the filter tips and one or more reagent racks.

In certain embodiments, the cylindrical magnet has magnetic poles symmetrically disposed along and around the longitudinal axis of the magnet. In other embodiments, the cylindrical magnet has opposing magnetic poles disposed at opposite longitudinal ends of the magnet. In yet other embodiments, the cylindrical magnet is an electromagnet.

In one embodiment, the one or more sample containers are sealed and configured to maintain a closed system following introduction of one or more reagent solutions.

In one embodiment, the system further comprises a reagent rack disposed in the housing, whereby the reagent rack comprises reagents stored in separate, sealed wells within the rack.

When in use, the sample container includes a magnetic stirrer and a plurality of beads configured so that when the sample container comprises cellular material and the cylindrical magnet is rotated about its longitudinal axis, the magnetic stirrer spins and agitates the beads to undergo chaotic mixing of the cellular material, resulting in sample homogenization and cell disruption.

In one embodiment, the beads comprise glass, plastic, ceramic material, minerals, metal or a combination thereof. In a particular embodiment, the beads are silica beads.

In one embodiment, the beads have diameters within the range of 10-1000 μm.

In one embodiment, the magnetic stirrer comprises a metal or an alloy. In a particular embodiment, the magnetic stirrer comprises stainless steel. In another embodiment, the magnetic stirrer comprises an alloy core coated with a polymer. In a particular embodiment, the magnetic stirrer comprises an alloy core coated with a polymer, whereby the alloy core comprises neodymium iron boron or samarium cobalt and/or where the polymer is PTFE or parylene.

In another aspect, an automated nucleic acid purification system includes the above-described features in combination with an automated pipetting system and one or more robotic arms configured to automatically dispense reagents into the one or more sample containers and dispose of sample materials and reagents in a predetermined manner. When in use, the automated purification system includes a plurality of the sample containers, each containing a stirrer and beads, a plurality of the filter tips and one or more reagent racks.

In another aspect, a method for purifying target molecules from a sample, includes the steps of (a) providing a sample purification system in accordance with the present disclosure; (b) placing a sample with a magnetic stirrer and a plurality of beads in a sample container; (c) placing the sample container on the sample container rack, (d) rotating the cylindrical magnet about its longitudinal axis so that the magnetic stirrer spins and agitates the beads to a degree sufficient to homogenize the sample and disrupt the cells in the sample to form a cell lysate; (e) flowing at least a portion of the cell lysate through a first opening of a filter tip so that target molecules in the cell lysate bind to the filter in the filter tip; (f) expelling an unbound portion of the cell lysate from the filter tip via the first opening, where the unbound portion passes through the filter at least two times before exiting the filter tip; and (g) eluting the target molecules bound to the filter by flowing an elution buffer in through the first opening of the filter tip and expelling the elution buffer from the filter tip via the first opening, wherein the elution buffer passes through the filter at least two times before exiting the filter tip.

In some embodiments, the target molecules are polynucleotide molecules. In one embodiment, the sample comprises sputum. In a particular embodiment, the sputum sample is suspected of containing *Mycobacterium Tuberculosis* (MTB) and the method further includes the step of amplifying the eluted polynucleotide molecules with primers specific for MTB and determining whether the polynucleotide molecules comprise MTB DNA.

In another embodiment, the method for purifying target molecules comprises the use of an automated purification system further comprising an automated pipetting system and one or more robotic arms configured to automatically dispense reagents into the one or more sample containers and dispose of sample materials and reagents in a predetermined manner. In this case, each of the above-described steps are repeated in each of a plurality of sample containers using an equivalent number of filter tips in combination with one or more reagent racks.

BRIEF DESCRIPTION OF DRAWINGS

The detailed description will refer to the following drawings in which:

FIG. 1 is a flow chart showing an embodiment of an integrated method for lysing cells and purifying nucleic acids therefrom.

DETAILED DESCRIPTION

Figure 2:
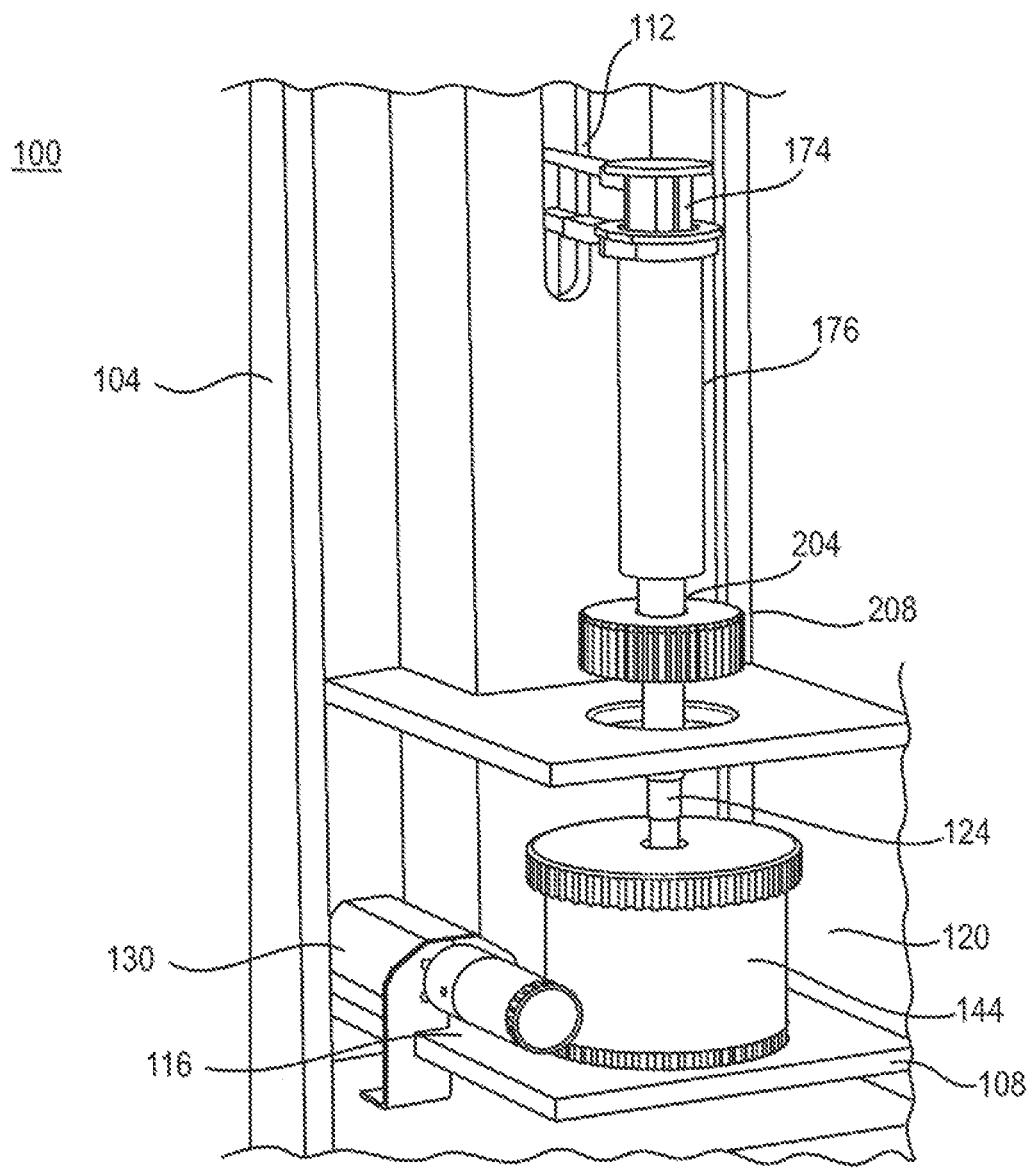
FIG. 2 depicts an exemplary single-channel nucleic acid purification system according to one embodiment.

In describing preferred embodiments of the present invention, specific terminology is employed for the sake of clarity.

However, the invention is not intended to be limited to the specific terminology so selected. It is to be understood that each specific element includes all technical equivalents which operate in a similar manner to accomplish a similar purpose.

FIG. 1 is a flow chart depicting exemplary process steps in an integrated method for lysing cells and purifying molecules of interest, such as nucleic acids or proteins therefrom. The method 10 includes placing a sample tube containing a liquid sample suspension, a magnetic stirrer and cell lysis beads on a sample rack in the proximity of a magnet (step 11); homogenizing the sample suspension by rotating the magnet at a speed sufficient to lyse cells in the sample suspension in the presence of the magnetic stirrer and cell lysis beads (step 13); flowing the homogenized sample suspension through a filter matrix under conditions that the molecules of interest bind to the filter matrix (step 15); washing the filter matrix (step 17) and eluting bound molecules of interest from the filter matrix (step 19). In some embodiments, the sample tube is pre-packed with a magnetic stirrer, and/or cell lysis beads, and/or reagents that facilitate cell lysis and/or preserve the integrity of the target molecules.

The liquid sample suspension is a sample suspended in liquid lysis medium. Exemplary samples may include biological samples, environmental samples or non-nature samples. Exemplary biological samples may include tissue samples, biological fluid samples, cell samples, fungal samples, protozoan samples, bacterial samples, and virus samples. Tissue samples include tissues isolated from any animal or plant. Biological samples include, but are not limited to, blood, cord blood, plasma, buffy coat, urine, saliva, sputum, NALC-treated sputum, nasopharyngeal swabs (NPS), nasopharyngeal aspirates (NPA), gastric aspirate, concentrated cough collection, cerebrospinal fluid, buccal, lavages (e.g. bronchial), pleural fluids, stool, and leukophoresis samples. Cell samples further include cultured cells, fresh or frozen cells and tissues from any cell sources, including fixed, paraffin-embedded (FFPE) tissues. Bacteria samples include, but are not limited to, cultured bacteria, isolated bacteria, and bacteria within any of the previously stated biological samples. Virus samples include, but are not limited to, cultured viruses, isolated viruses, and viruses within any of the previously stated biological samples. Environmental samples include, but are not limited to, air samples, water samples, soil samples, rock samples and any other samples obtained from a natural environment. The artificial samples include any sample that does not exist in a natural environment. Examples of "artificial samples" include, but are not limited to, purified or isolated materials, cultured materials, synthesized materials and any other man-made materials.

The liquid lysis medium can be isotonic, hypotonic, or hypertonic. In some embodiments, the liquid lysis medium is aqueous. In certain embodiments, the liquid lysis medium contains a buffer and/or at least one salt or a combination of salts. In some embodiments, the pH of the liquid lysis medium ranges from about 5 to about 8, from about 6 to 8, or from about 6.5 to about 8.5. A variety of pH buffers may be used to achieve the desired pH. Suitable buffers include, but are not limited to, Tris, MES, Bis-Tris, ADA, ACES, PIPES, MOPSO, Bis-Tris propane, BES, MOPS, TES, HEPES, DIPSO, MOBS, TAPSO, HEPPSO, POPSO, TEA, HEPPS, Tricine, Gly-Gly, Bicine, and a phosphate buffer (e.g., sodium phosphate or sodium-potassium phosphate, among others). The liquid lysis medium may comprise from about 10 mM to about 100 mM buffer, about 25 mM to about 75 mM buffer, or from about 40 mM to about 60 mM buffer, among others. The type and amount of the buffer used in the liquid medium can vary from application to application. In some embodiments, the liquid lysis medium has a pH of about 7.4, which can be achieved using about 50 mM Tris buffer. In some embodiments the liquid lysis medium is water.

Eukaryotic cells, prokaryotic cells, and/or viruses may be suspended at any suitable concentration. Preferably, the samples contain cells suspended in a liquid medium at a concentration that does not interfere with the movement of the magnetic stirrer. In some embodiments, eukaryotic cells and/or prokaryotic cells are suspended at a concentration ranging from 1 to $1\times10^{10}$ cells/ml, 1 to $1\times10^{5}$ cells/ml, or $1\times10^{3}$ to $1\times10^{4}$ cells/ml, among others. In some embodiments, virus particles are suspended in a concentration ranging from 1 to $1\times10^{13}$ particles/ml, 1 to $1\times10^{10}$ particles/ml, or $1\times10^{5}$ to $1\times10^{7}$ particles/ml.

In certain preferred embodiments, the sample is suspected of containing MTB. In one embodiment, the sample is a nasopharyngeal aspirate. In another embodiment, the sample is a nasopharyngeal swab.

As used herein, the term "cells" refers to eukaryotic cells, prokaryotic cells, viruses, endospores or any combination thereof Cells thus may include bacteria, bacterial spores, fungi, virus particles, single-celled eukaryotic organisms (e.g., protozoans, yeast, etc.), isolated or aggregated cells from multi-cellular organisms (e.g., primary cells, cultured cells, tissues, whole organisms, etc.), or any combination thereof, among others.

The terms "sample" refer to any material that contains the target molecules or is suspected of containing the target molecules.

The term "nucleic acids" refers to individual nucleic acids and polymeric chains of nucleic acids, including DNA and RNA, whether naturally occurring or artificially synthesized (including analogs thereof), or modifications thereof, especially those modifications known to occur in nature, having any length.

The term "sample container" refers to an elongated, generally tubular container or vial for securing and/or processing a sample for purification of nucleic acid or receiving reagents in combination with a processed sample. The sample containers need not be cylindrical and may be slightly conical along their entire length or along a portion thereof.

The term "lyse" with respect to cells means disruption of the integrity of at least a fraction of the cells to release intracellular components, such as nucleic acids and proteins, from the disrupted cells.

The term "homogenize" means blending or vortexing (diverse elements e.g. stool, tissue, sputum, saliva) into a uniform mixture.

The terms "closed system" or "closed container" refers to tubes or containers that are sealed and operate in a substantially, if not totally, closed manner to impede or prevent the introduction of exogenous or external materials into (or out of) the tube or container during processing. Components of the closed systems or containers can be pre-sterilized prior to use at a manufacture site, sterilized at the point of use, and/or sterilized after a respective closed system is assembled and closed prior to use.

The term "single-use disposable" refers to a component that is not reused. That is, after completing its intended use, i.e., processing or production of a target sample or sample(s), it is disposed of.

As used herein, the terms "monolith adsorbent" or "monolithic adsorbent material" refer to a porous, three-dimensional adsorbent material having a continuous interconnected pore structure in a single piece, which may comprise a rigid, self-supporting substantially monolithic structure. A monolith is prepared, for example, by casting, sintering or polymerizing precursors into a mold of a desired shape. The term "monolith adsorbent" or "monolithic adsorbent material" is meant to be distinguished from a collection of individual adsorbent particles packed into a bed formation or embedded into a porous matrix, in which the end product comprises individual adsorbent particles. Porous monolithic polymers are a new category of materials developed during the last decade. In contrast to polymers composed of very small beads, a monolith is a single, continuous piece of a polymer prepared using a simple molding process. The term "monolith adsorbent" or "monolithic adsorbent material" is also meant to be distinguished from a collection of adsorbent fibers or fibers coated with an adsorbent, such as filter papers or filter papers coated with an adsorbent.

In one aspect, the present application provides an integrated sample purification system comprising housing, a sample container rack, a filter tip rack, and a cylindrical magnet. The sample container rack and the filter tip rack are disposed in the housing. The sample container rack is configured to hold one or more sample containers, the filter tip rack is configured to hold one or more filter tips. The cylindrical magnet is adjacent to and external to the sample container rack, and is rotatably driven about a central, longitudinal axis of the magnet by an electric motor disposed in the housing.

FIG. 2 depicts an exemplary single-channel sample purification system 100 according to one embodiment. The system 100 in FIG. 2 includes housing 104, a sample container rack 108, a filter tip actuator/rack 112, and a cylindrical magnet 116. The sample container rack 108 and the filter tip rack 112 are disposed in the housing 104. A sample container rack or stand 108 holds the sample container 120. The filter tip actuator/rack 112 in FIG. 2 is configured to hold a filter tip 124 attached to syringe 176, which is configured so that a syringe plunger 174 in the syringe 176 moves up and down to aspirate and dispense liquid through the filter tip 124. The plunger 174 is connected to an actuator in the rack 112 that controls the plunger movement. The cylindrical magnet 116 is adjacent to and external to the sample container rack 108, and is rotated about a central, longitudinal axis of the magnet 116 by an electric motor 130 disposed in the housing 104.

Figure 3:
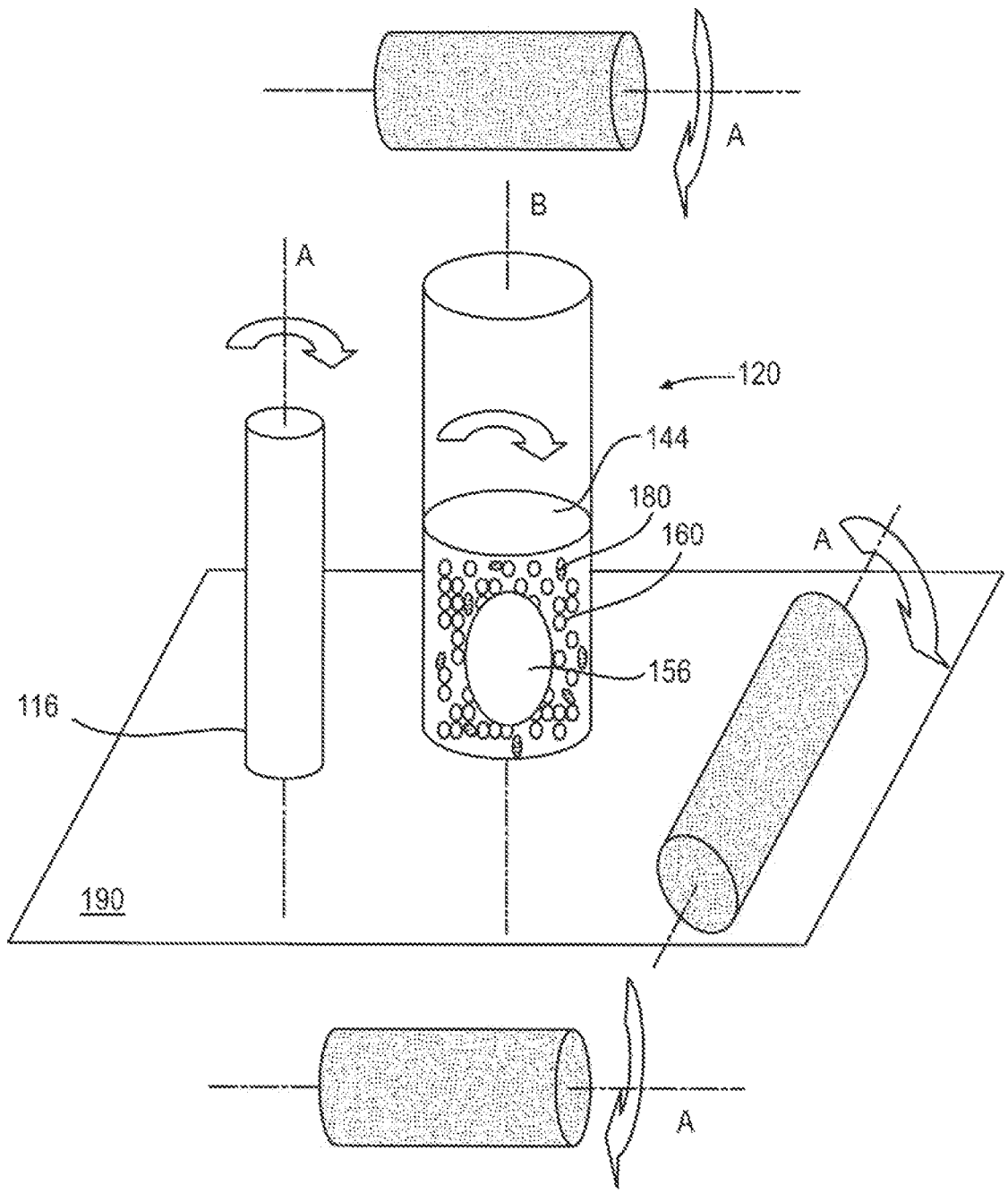
FIG. 3 shows exemplary positions for placement of the magnet relative to a sample lysis chamber.

Each sample container 120 may contain one or more lysis chambers for lysing cells in a sample. Preferably, the sample container(s) 120 (and other system components) are sealed and configured to maintain a closed system before and after introduction of samples 144 and/or one or more reagent solutions. The container 120 may be sealed with a lid, cap, or cover. The sample container 120 can be made with any suitable material, size, and shape. In certain embodiments, the container 120 is made of plastic. Preferably, the interior surface of the container 120 is chemically inert. The sample container 120 may, for example, be in the shape of a urine collection cup, a micro centrifuge tube (e.g., an Eppendorf tube), a centrifuge tube, a vial, a microwell plate etc. In some embodiments, the container 120 contains a single compartment/chamber for holding cells 180, beads 160, and a stirrer 156, as shown in FIG. 3. In some embodiments, a given container 120 may include a plurality of discrete compartments/chambers (e.g., an array of wells), each capable of holding mixtures of cells 180, beads 160, and magnetic stirrers 156 in isolation from one another. In some embodiments, the sample container 120 is pre-packed with a magnetic stirrer and/or cell lysis beads, as well as chemicals and/or enzymes that facilitate cell lysis and preserve the bioactivity of the target molecules.

The system 100 may comprise a plurality of sample containers 120, a plurality of filter tips 124, one or more reagent racks 132 or a combination thereof. The sample container rack 108 may be configured to hold multiple sample containers 120 and can be placed on a support surface of the housing 104 for simultaneous processing of multiple samples 144. Likewise, the filter tip rack 112 may be configured to hold multiple filter tips 124 and can be placed on a support surface of the housing 104 for simultaneous processing of multiple samples 144. The sample container rack 108 may also be used as holder of the samples 144 for storage purpose. For example, multiple sample containers 120 may be placed in the sample container rack 108 and stored in a refrigerator or freezer prior to analysis.

Referring now to FIG. 3, when in use, the sample containers 120 and the cylindrical magnet 116 are configured such that when the cylindrical magnet 116 is rotated about its longitudinal axis, the magnetic stirrer 156 in the sample container spins and agitates the beads 160 in sufficient force to cause disruption and homogenization of cells 180.

The cylindrical magnet 116 may have a number of magnet geometries or configurations. In one embodiment, the magnet has magnetic poles (i.e., north and south) symmetrically disposed along and around the longitudinal axis of the magnet. The magnet may have a plurality of opposing poles alternating around and about the longitudinal axis, preferably an even number, such as 2, 4, 6, 8, 10, 12, 14, 16, 18, 20, 22 and 24. In other embodiments, the cylindrical magnet has opposing magnetic poles disposed at opposite longitudinal ends of the magnet. In yet other embodiments, the cylindrical magnet is an electromagnet.

The magnet 116 may be rotated above, below or by the side of the sample container 120 about an axis that passes through the center of the magnet 116. In certain embodiments, the sample container(s) 120 are placed vertical to the surface on which the sample container(s) 120 reside on and the magnet 116 is rotated about an axis that is also vertical to the surface on which the sample container(s) 120 reside. In other embodiments, the sample container(s) 120 are placed vertical to the surface on which the sample container(s) 120 reside on and the magnet 116 is rotated about an axis that is parallel to the surface on which the sample container(s) 120 reside. In yet other embodiments, the sample container(s) 120 are placed vertical to the surface on which the sample container(s) 120 reside on and the magnet 116 is rotated about an axis that forms an angle with the surface on which the sample container(s) 120 reside. The angle is greater than 0 degree but smaller than 180 degrees.

FIG. 3 shows the relative positions of the magnet 116 relative to a sample container 120. The magnet 116 rotates about an axis A and causes a magnetic stirrer 156 in the sample container 120 to rotate in the same direction along an axis B that is parallel to axis A. While only one axis B is shown in FIG. 3, a person skilled in the art would understand that the magnetic stirrer 156 may rotate about other B axes that are parallel to other A axes shown in the figure. The rotating magnetic stirrer 156 collides with beads 160 and lyses cells 180 in the process. The magnet 116 may be positioned alongside, above, below or diagonally from the sample container 120, which is placed vertical to the surface 190 on which the chamber(s) (or the holder of the sample container 120.

The sample container 120, and particularly the sample 144, beads 160, and magnetic stirrer 156, are located within an operational range of a varying magnetic field. For example, the sample container 120 may be located within an operational range of a rotating magnetic field, e.g., by placing the container 120 adjacent to or in the proximity of the cylindrical magnet 116. The varying magnetic field drives motion of the magnetic stirrer 156, such as rotational motion, reciprocation, or a combination thereof, among others, which in turn drives motion of the beads 160, the cells, and the liquid medium. In some embodiments, the sample suspension 144 is stirred with the magnetic stirrer 156 at a rotational speed and for durations sufficient to lyse the cells inside the container 120. The appropriate rotation speed and duration are application dependent and can be empirically determined by a person of ordinary skill in the art. Generally speaking, the rotational speed sufficient to lyse the cells, is determined by factors such as the type of cells, the concentration of sample suspension 144, the volume of the sample suspension, the size and shape of the magnetic stirrer 156, the amount/number, size, shape and hardness of the cell lysis beads 160, and the size and shape of the sample container 120.

In certain embodiments, the magnetic stirrer 156 is rotating at a speed between 1000-6000 rpm, preferably about 5000 rpm, for a time period between 1-600 seconds, preferably about 90-120 seconds. In certain embodiments, a sample container 120 (e.g., in the shape of a urinalysis cup or tube) is placed in a rack on a magnetic stirrer and is stirred at the highest speed setting (>1000 rpm). In other embodiments, the sample container 120 is a well in a microplate such as an ELISA plate. In other embodiments, the sample container 120 is a cylinder shaped container with a sample inlet and a sample outlet.

In certain embodiments, the speed of rotation of the magnetic stirrer 156 is increased to increase lysis efficiency and reduces the time required to achieve lysis. In certain other embodiments, the speed of rotation is regulated so that only certain types of cells are lysed. For example, in a sample suspension 144 containing multiple types of cells 180, the stirrer 156 may rotate at a first speed to lyse a first set of cells and then rotate at a second speed to lyse a second set of cells. In other embodiments, the container 120 is coupled to a temperature regulation module that controls the temperature of the sample suspension 144 before, during and/or after the lysing process. In certain embodiments, the temperature of the sample suspension 144 is maintained at 2°–8° C. In some embodiments, the sample suspension 144 is heated to 40°–80° C., 50°–70° C., or about 60° C., before, during and/or after the lysing process (e.g., during the rotation of the magnetic stirrer).

The magnetic stirrer 156 may be made of metal or metal alloy. In one embodiment, the magnetic stirrer 156 is made of stainless steel. In other embodiments, the magnetic stirrer 156 is made from an alloy core coated with a chemically inert material, such as polymer, glass, or ceramic (e.g., porcelain). Exemplary alloy core materials include neodymium iron boron and samarium cobalt. Exemplary coating polymers include biocompatible polymers, such as PTFE and parylene.

The magnetic stirrer 156 can be of any shape and should be small enough to be placed into the sample container 120 and to move or spin or stir within the container 120. The magnetic stirrer 156 can be a bar-shaped, cylinder-shaped, cross-shaped, V-shaped, triangular, rectangular, rod or disc-shaped stirrer 156, among others. In some embodiments, the magnetic stirrer 156 has a rectangular shape. In some embodiments, the magnetic stirrer 156 has a two-pronged tuning fork shape. In some embodiments, the magnetic stirrer 156 has a V-like shape. In some embodiments, the magnetic stirrer 156 has a trapezoidal shape. In certain embodiments, the longest dimension of the stirrer 156 is slightly smaller than the diameter of the container (e.g., about 75-95% of the diameter of the container).

The cell lysis beads 160 can be any particle-like and/or bead-like structure that has a hardness greater than the hardness of the cells. The beads 160 may be made of plastic, glass, ceramic, mineral, metal and/or any other suitable materials. In certain embodiments, the beads 160 may be made of non-magnetic materials. The beads 160 may be rotationally symmetric about at least one axis (e.g., spherical, rounded, oval, elliptic, egg-shaped, and droplet-shaped particles). In certain embodiments, the beads 160 have polyhedron shapes. In other embodiments, the beads 160 are irregularly shaped particles. In some embodiments, beads 160 are particles with protrusions. The beads 160 may have diameters in the range of 10-1,000 μm, 20-400 μm, or 50-200 μm, among others. The amount of beads 160 added to each lysis container may range from about 1-10,000 mg, 1-1000 mg, 1-100 mg, 1-10 mg, among others.

Figure 4:
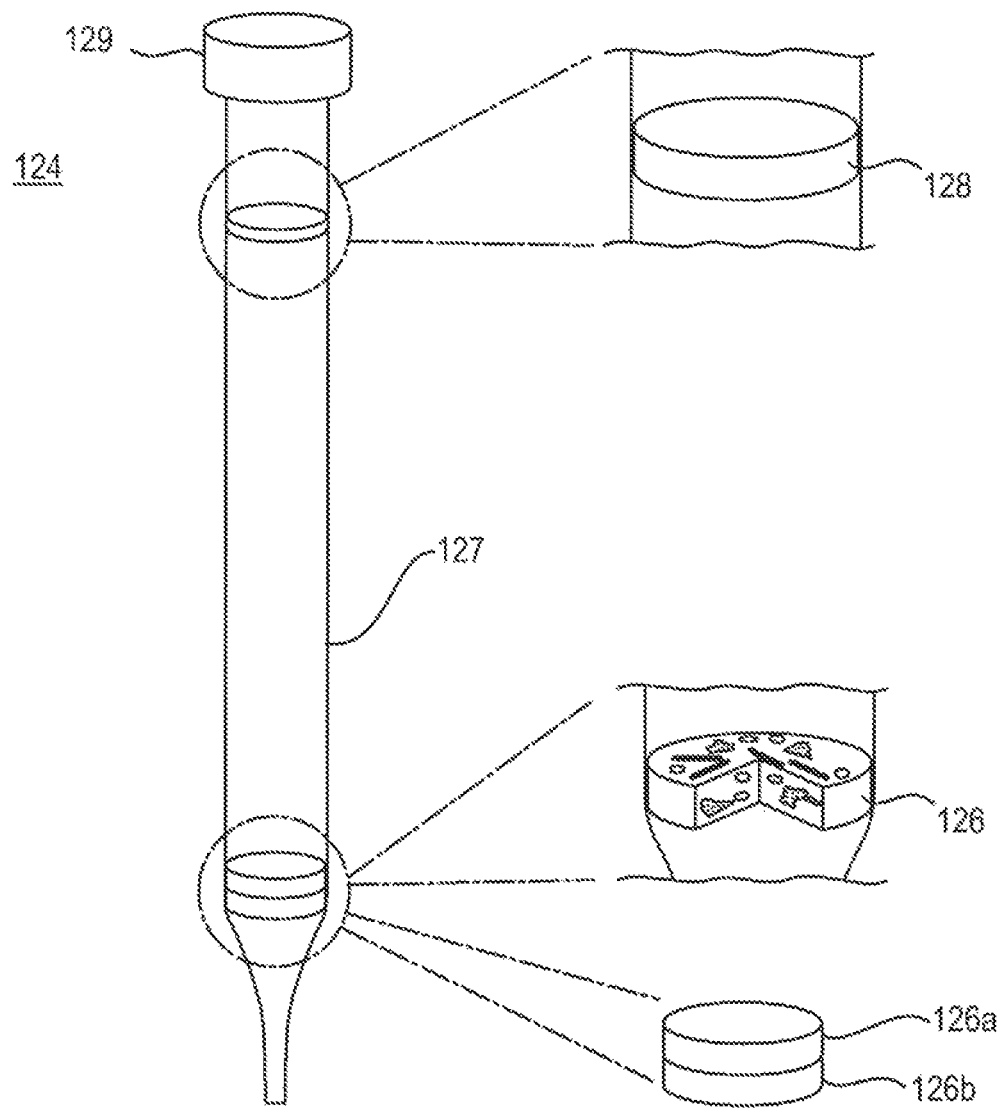
FIG. 4 depicts an exemplary pipette filter tip.

After the cells have been lysed, the cell lysate is drawn into a suitable filter tip 124 to allow for the nucleic acids to bind to the filter matrix 126 therein (see FIG. 4). Typically, the lysate is passed through the filter matrix 126 at least two times before expelling the unbound portion out the same end of the filter tip 124. At this point, the bound nucleic acids in the filter tip 124 can be stored in a sealed container for further analysis at another time. Alternatively, the bound nucleic acids can be eluted from the filter tip using a suitable elution buffer as further described below.

FIG. 4 depicts an exemplary filter tip. The filter tip 124 comprises a porous monolithic binding filter matrix 126 inserted into a pipette tip 127. The monolith binding filter matrix 126 comprises a monolith adsorbent or monolithic adsorbent material. The porous monolithic material binds specifically to nucleic acids and is composed of a rigid, self-supporting, substantially monolithic structure. In some embodiments, the porous monolithic material does not include additional materials that provide nucleic acid affinity. In some preferred embodiments, the porous monolithic material is a glass-based monolithic material such as a glass frit. In certain embodiments, the glass frit is a sintered glass frit. The porosity of the porous monolithic material, such as a glass frit or sintered glass frit, is application dependent. In general, the porous monolithic material should have a porosity that allows for a desired sample flow rate for a particular application and is capable of retaining nucleic acids in a desired size range. In some embodiments, the monolith binding filter matrix 126 is a glass frit consisting of two sections (126a and 126b) with different porosity.

In some embodiments, the porous monolithic material is a glass frit or sintered glass frit having a porosity (i.e., an average pore size) in the range of 2-400 micron, 2-300 micron, 2-220 micron, 2-200 micron, 2-180 micron, 2-160 micron, 2-140 micro, 2-120 micro, 2-100 micron, 2-80 micron, 2-60 micron, 2-40 micron, 2-20 micron, 2-16 micron, 2-10 micron, 2-5.5 micron, 4-400 micron, 4-300 micron, 4-220 micron, 4-200 micron, 4-180 micron, 4-160 micron, 4-140 micro, 4-120 micro, 4-100 micron, 4-80 micron, 4-60 micron, 4-40 micron, 4-20 micron, 4-16 micron, 4-10 micron, 4-5.5 micron, 10-400 micron, 10-300 micron, 10-220 micron, 10-200 micron, 10-180 micron, 10-160 micron, 10-140 micro, 10-120 micron, 10-100 micron, 10-80 micron, 10-60 micron, 10-40 micron, 10-20 micron, 10-16 micron, 16-400 micron, 16-300 micron, 16-220 micron, 16-200 micron, 16-180 micron, 16-160 micron, 16-140 micro, 16-120 micro, 16-100 micron, 16-80 micron, 16-60 micron, 16-40 micron, 40-400 micron, 40-300 micron, 40-220 micron, 40-200 micron, 40-180 micron, 40-160 micron, 40-140 micro, 40-120 micro, 40-100 micron, 40-80 micron, 40-60 micron, 100-400 micron, 100-300 micron, 100-220 micron, 100-200 micron, 100-180 micron, 100-160 micron, 100-140 micro, 100-120 micro, 160-400 micron, 160-300 micron, 160-220 micron, 160-200 micron, 160-180 micron, 200-400 micron, 200-300 micron, or 200-220 micron. In other embodiments, the porous monolithic material is a glass frit or sintered glass frit having two sections (126*a* and 126*b*) of different porosity. Each section may have a porosity in a range described above (e.g. a 4-10 micron section and a 16-40 micron section, or a 16-40 micron section and a 100-160 micron section).

In some embodiments, the filter has a thickness in the range of 1=30 mm, 1-25 mm, 1-20 mm, 1-15 mm, 1-10 mm, 1-8 mm, 1-6 mm, 1-4 mm, 2-30 mm, 2-25 mm, 2-20 mm, 2-15 mm, 2-10 mm, 2-8 mm, 2-6 mm, 2-4 mm, 4-30 mm, 4-25 mm, 4-20 mm, 4-15 mm, 4-10 mm, 4-8 mm, 4-6 mm, 6-30 mm, 6-25 mm, 6-20 mm, 6-15 mm, 6-10 mm, 6-8 mm, 8-30 mm, 8-25 mm, 8-20 mm, 8-15 mm, 8-10 mm, 10-30 mm, 10-25 mm, 10-20 mm, 10-15 mm, 15-30 mm, 15-25 mm, 15-20 mm, 20-30 mm, 20-25 mm, or 25-30 mm.

In some embodiments, the porous monolithic material may be modified with one or more materials having affinity to the molecules of interest, such as polynucleotide, protein, lipid or polysaccharide. In some embodiments, the porous monolithic material may be modified with one or more materials having affinity to nucleic acids.

In some embodiments, the filter is made of a porous glass monolith, a porous glass-ceramic, or porous monolithic polymers. In some embodiments, the porous glass monolith is produced using the sol-gel methods described in U.S. Pat. Nos. 4,810,674 and 4,765,818, which are hereby incorporated by reference. Porous glass-ceramic may be produced by controlled crystallization of a porous glass monolith. In preferred embodiments, the porous glass monolith, porous glass-ceramic or porous monolithic polymer is not coated or embedded with any additional materials, such as polynucleotides or antibodies, to improve its binding affinity to nucleic acids.

In some preferred embodiments, the filter is made of a finely porous glass frit through which a liquid sample may pass. The porous glass fit is not coated or embedded with any additional materials, such as polynucleotides or antibodies, to improve its affinity to the nucleic acids or other molecules of interest. Suitable substrates for purifying nucleic acids include porous glass frits made of sintered glass, which are formed by crushing beads in a hot press to form a single monolithic structure. The uniform structure of the frit provides predictable liquid flow inside the frit and allows the eluent to have similar fluid dynamics as the sample flow. The predictable liquid flow allows for high recovery during the elution process.

Although the filter matrix 126 is typically placed in a pipette tip 127, it may also be fitted into columns, syringes or other housings of different volumes and shapes. Liquid solutions may be passed through the filter matrix 126 using various devices, including manual or automatic pipettes, syringes, syringe pumps, hand-held syringes, or other types of automated or manual methods for moving liquid across the filter matrix 126.

Figure 5A:
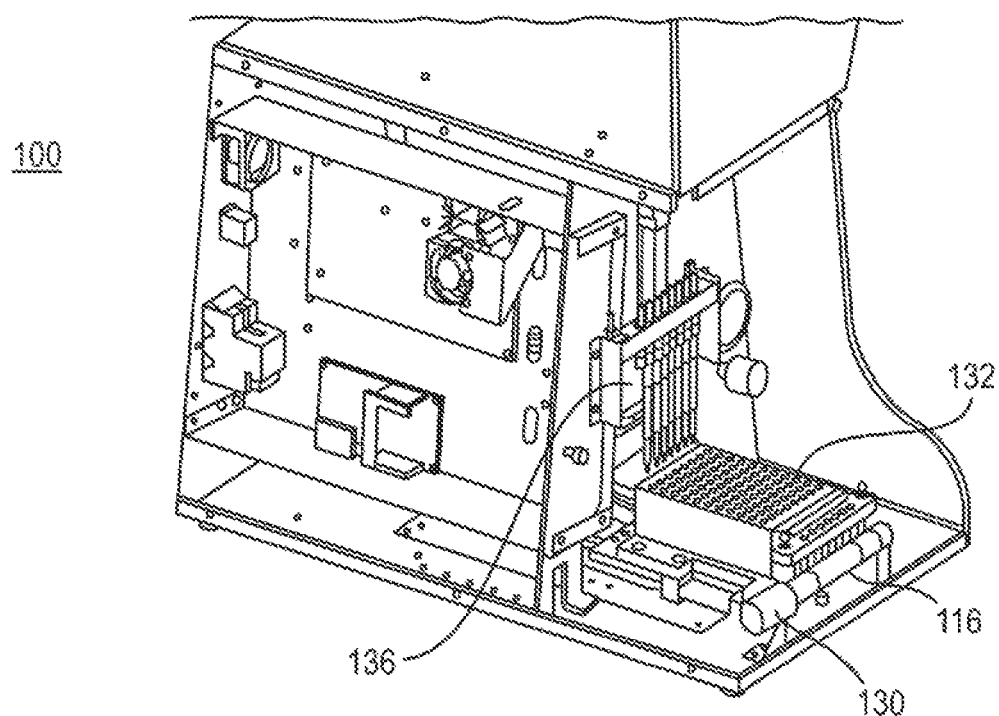
FIGS. 5A and 5B are schematic illustrations depicting an automated 8-channel nucleic acid purification system according to another embodiment.
Figure 5B:
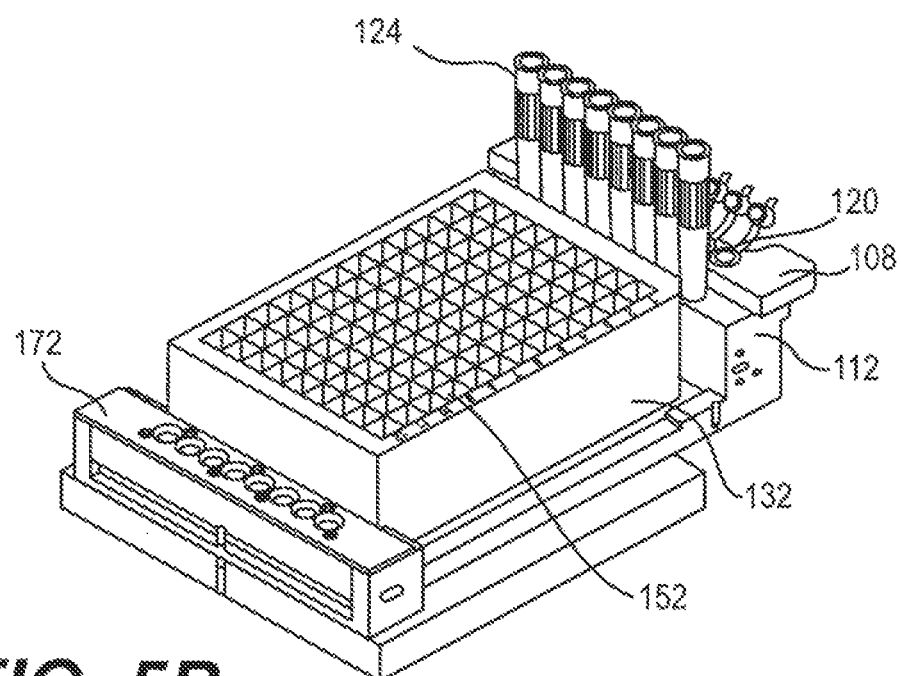

As shown in FIGS. 5A and 5B, the system may further include one or more reagent racks 132 disposed in a housing.

The reagent rack 132 is configured to hold one or more reagents. The reagent rack 132 may be in the form of a tray into which reagents can be poured when ready for use. In this case, the reagents may be poured into the tray to facilitate receipt of the reagents into multiple pipette tips for delivery to multiple sample wells during the processing of samples 144. Alternatively, the reagent rack 132 may be in the form of a block or multiwell plate (e.g., 24-well, 96-well etc.) comprising a plurality of wells 152, whereby each of the plurality of wells is configured to hold any of the reagents for processing a separate sample 144. In certain embodiments, the wells 152 may be prefilled with the reagents and sealed within the rack 132. In some embodiments, the rack 132 is located near the sample container rack 108 and/or the filter tips rack 112 (FIG. 5B).

The sample purification system 100 may be manually operated or it may be configured to be run in a semi-automated or fully automated matter by programmable logic. In certain embodiments, the system may further include an automated pipetting system 136 (FIG. 5A) and one or more robotic arms (not shown) configured to automatically dispense reagents from one or more reagent racks 132 into a plurality of sample containers 120 and dispose of sample materials and used reagents into suitable disposal receptacles 172 in a predetermined, computer controlled manner (FIG. 5B).

In one mode of operation, reagent racks 132 are in the form of multiwell plates (e.g., 24-well, 96-well etc.). Preferably, the mixtures are mixed by use of automated liquid handling as this will reduce the amount of work that needs to be done in order to prepare the mixtures to be investigated. Automated sampling protocols may also be performed by means of robotics using equipment and methods known in the art.

Any suitable machinery or equipment may be used to move the samples 144 through the automated purification system 100 and its various processing steps. For example, the systems 100 employed herein can use a variety of robotics known in the art to automate the movement of samples 144, reagents and other system components. Exemplary robotic systems have capabilities to move samples on one, two, or three axes and/or to rotate samples about one, two, or three axes. Exemplary robotics move on a track which may be situated above, below, or beside a workpiece. Typically a robotic component includes a functional component, e.g., a robotic arm capable of griping and/or moving a workpiece, inserting a pipettor, dispensing a reagent, aspirating, etc. A "robotic arm", as used herein, means a device, preferably controlled by a microprocessor, that physically transfers samples 144, containers 120, filter tips 124, sample container racks 108, filter tips racks 112 and reagent racks 132 from one location to another. Each location can be a unit in the automated purification system 100. Software for the control of robotic arms is generally available from the manufacturer of the arm.

Robotics may be translated on a track, e.g., on the top, bottom, or side of a work area, and/or may include articulating segments which allow the arm to reach different locations in the work area. Robotics may be driven by motors known in the art, which may be, for example electrically, pneumatically, or hydraulically powered. Any suitable drive control system may be used to control the robotics, such as standard PLC programming or other methods known in the art. Optionally the robotics include positional feedback systems that optically or mechanically measure position and/or force, and allow the robot to be guided to a desired location. Optionally, robotics also include position assurance mechanisms, such as mechanical stops, optical markers or laser guides, that allow particular positions to be repeatedly obtained.

Exemplary automated sampling protocols may utilize, for example, an Eppendorf epMotion 5070, epMotion 5075, Hamilton STARlet, STAR and STARplus liquid handling robots. Such protocols may be adapted for RNA isolation, genomic DNA isolation from whole blood, tissues, saliva, swabs, as well as circulating cell-free DNA such as circulating tumor DNA and circulating fetal DNA extraction and enrichment from maternal plasma.

Methods for Purifying Nucleic Acids

In another aspect, a method for purifying nucleic acids from a sample, includes the steps of (a) providing a nucleic acid purification system in accordance with the present disclosure; (b) introducing into a sample container the sample, a magnetic stirrer and a plurality of beads; (c) rotating the cylindrical magnet about its longitudinal axis so that the magnetic stirrer spins and agitates the beads to undergo chaotic mixing of cellular contents to a degree sufficient for homogenizing the sample and disrupting the cells in the sample to form a cell lysate; (d) flowing at least a portion of the cell lysate through a first opening of a filter tip so that nucleic acids in the cell lysate bind to the filter in the filter tip; (e) expelling an unbound portion of the cell lysate from the filter tip via the first opening, where the unbound portion passes through the filter at least two times before exiting the filter tip; and (f) eluting the nucleic acids bound to the filter by flowing an elution buffer in through the first opening of the filter tip and expelling the elution buffer from the filter tip via the first opening, wherein the elution buffer passes through the filter at least two times before exiting the filter tip.

Any mode of performing the method according to the present application can be employed, including fully manual, semi-automated or fully automated protocols. However, the attributes, adaptability, simplicity and workflow of the filter tip allow for it to be readily adapted, automated, and effective for a number of clinical sample matrices, input sample volumes, and liquid handling systems. Thus, in a preferred embodiment, the mode of operation includes some kind of automation. In one embodiment, the method for purifying nucleic acids comprises an automated pipetting system and one more robotic arms configured to automatically dispense reagents into one or more sample containers and dispose of sample materials and reagents into suitable disposable receptacles in a predetermined manner. In this case, each of the above-described steps are repeated in each of a plurality of sample containers using an equivalent number of filter tips in combination with one or more reagent racks.

Samples suspected of containing MTB present a potential risk to the user. Accordingly, the sample may be pre-treated by heating and/or inclusion of reagents suitable for inactivating microbes present in the sample to mitigate this risk. Inactivation of microbes, such as MTB, may be carried out by heating (e.g., 90° C., 5 min.) to denature active proteins, enzymatic digestion of cell wall structures, mechanical disruption to physically disrupt or inactivate the cells, chemical treatment or a combination thereof.

Chemical inactivation offers the potential to reduce or eliminate the need for heat. When processing a sample for culturing, simple reagents are used to digest the sputum and disinfect the sample. For culturing, it is important to inactivate other flora present in the sputum sample, so that MTB can grow without being overtaken by other faster-growing bacteria. The decontamination or inactivation step, which may use reagents such as sodium hydroxide (e.g., 3-5%) or cetylpyridinium chloride, is preferably selected to inactivate all other bacteria, but keep MTB cells with a thicker, more robust cell wall, intact and alive. However, depending on the method used, 20 to 90% of the MTB cells can be killed during this process. With regard to nucleic acid purification, however, the MTB cells do not need to be alive or intact, as long as the bacterial genomic DNA is still able to be amplified.

Inactivating reagents are preferably chosen to allow for limited dilution of the sample and/or low pH for compatibility to silica binding. These reagents may be added to the sample at the time of collection. In some embodiments, hydrogen peroxide, alcohols, such as ethanol and o-phenylphenol (e.g., 0.2-0.5%) may be used as primary active ingredients. Hydrogen peroxide ($H_2O_2$) may be used as a chemical sterilant from 6-25% concentrations and is very stable in solution. When mixed with 0.85% phosphoric acid, $H_2O_2$ is active at low pH. Ethanol alone (e.g., at 95%) can inactivate MTB in sputum or water in 15 seconds. 0-phenylphenol, an agricultural fungicide, is used at 0.1-0.41% with either ethanol or isopropanol in PHENO-CEN, SRAY-PAK, and CLIPPERCIDE spray disinfectants. In addition, 0-phenylphenol may be used at low reagent to sample ratios at room temperature in 15 min and it may be used in combination with ethanol or isopropanol or with 6.65% 2-Benzyl-4-chlorophenol in Low pH Phenolic 256 (50%-100%)

The volume ratio of inactivating reagents to sample volume will typically range from about 0.1:1 to 3:1.

Inactivation of microbes in the primary specimen container is important for providing a BSL-1 compatible workflow (i.e., the workflow does not require a biosafety cabinet). Many protocols involve sample transfer prior to disinfection, a practice which can produce aerosols, and infect the user. Accordingly, BSL-1 compatibility requires careful attention to sample transfers prior to disinfection, particularly those that can produce aerosols and infect the user.

Depending on the nature of the sample, the sample may be initially liquefied to reduce its viscosity and heterogeneity for consistent sample processing. Sputum samples present a particular challenge. MTB in sputum is one of the most challenging cell and sample types to process due to the lipid-rich hydrophobic cell wall of acid fast bacilli and the viscous, heterogeneous nature of sputum. Standard extraction methods for sputum typically start with a process of sedimentation, which often involves the treatment with N-acetyl-L-cysteine (NALC) and sodium hydroxide (NaOH) followed by centrifugation, decanting, and re-suspension. Accordingly, when processing highly viscous samples, such as sputum, the sample may be subjected to chemical treatment in order to reduce the viscosity so that subsequent processing steps (e.g., MagVor) are not impeded. Exemplary mucolytic reagents for addition to the sample include, but are not limited to NALC, zephiran-trisodium phosphate (Z-TSP), benzalkonium, and Primestore™. (Longhorn Vaccines & Diagnostics, San Antonio Tex.), which contains a special formulation to lyse bacteria and stabilize RNA and DNA. In one embodiment, liquefaction of samples by chemical treatment with mucolytic agents is carried out for 20 minutes at 60° C. Patient sputum sample may be typically collected in volumes between 1-10 ml, 5-10 ml or greater.

Sputum has a viscosity range from about 100-6,000 cP (mPa's) with a shear rate at 90 $s^{-1}$. The viscosity, measured in mPas, is determined by shear strength divided by shear rate. Preferably, the sample is liquefied to reduce the viscosity of sputum by at least 50%, at least 60%, at least 70%, at least 80%, at least 90%, at least 95%, or at least 99%.

When processing a sample, at least one magnetic stirrer and a plurality of cell lysis beads are present in the sample container. A user may simply add a sample suspension into the sample container, place the sample container adjacent to the cylindrical magnet, and stir the sample suspension by rotating the magnet at a speed sufficient for the rotating magnetic field to cause rotation of the magnetic stirrer and stirring of the cell lysis beads in the sample container in a manner sufficient to homogenize and lyse the cells.

The sample suspension, cell lysis beads and the magnetic stirrer may be placed into the sample container in any order. In some embodiments, the sample suspension is added to the sample container before the cell lysis beads and the magnetic stirrer. In other embodiments, the cell lysis beads and/or the magnetic stirrer are placed into the sample container before collection of the sample.

In certain embodiments, lysing of particular cell types can be facilitated by adding additives to the sample suspension prior to and/or during the stirring step. Examples of additives include enzymes, detergents, surfactants and other chemicals such as bases and acids. It has been found that alkaline conditions (e.g., 10 mM NaOH) may enhance the lysis efficiency during stirring for certain types of cells. The sample suspension may also or alternatively be heated during stirring to enhance the lysis efficiency. Additives, however, can be detrimental to downstream processing steps including nucleic acid amplification and detection and should be eliminated when possible to simplify the process.

The stirrer/beads combination provides many advantages over conventional lysing methods. The stirrer/beads method is much faster than chemical and enzymatic approaches, and provides improved cell or virus lysis over many other types of physical lysis methods. The stirrer/beads method is also amenable to automation using robotics and/or microfluidics. The cylindrical magnet is reusable, doesn't require precise alignment with the container, and can drive a plurality of chambers. The magnetic stirrer is low-cost, enabling its use in a single-use disposable.

Following the MagVor step, a suitable binding buffer containing one or more chaotropic agents are added to the sample container to facilitate binding of nucleic acids to the filter matrix 126. BOOM chemistry, or chaotropic binding of nucleic acids to silica, is most efficient when the solution pH is less than 7. In this case, high ionic strength solutions containing lithium or sodium chloride, or guanidine-based ions are typically combined with an aliphatic alcohol, such as ethanol or isopropanol to "salt out" the DNA and promote nucleic acid binding, respectively. A suitable binding buffer is used at a concentration so that when it is added to the processed sample, the resultant volume is within the range of the volumetric capacity of the filter tip. This reduces the number of aspirate and dispense cycles, and thus, the total processing time.

In certain embodiments, the binding buffer is added to the sample and incubated for 10 minutes at 60° C. following MagVor. In other embodiments, chaotropic agents and aliphatic alcohols are included in the liquefaction step, prior to the MagVor step. In other embodiments, the inactivation, homogenization and lysis steps are carried out in a single step in as little as 15 minutes.

Exemplary chaotropic agents include, but are not limited to chaotropic salts, such as guanidinium thiocyanate, guanidine isothiocyanate, guanidine hydrochloride, guanidinium chloride urea, thiourea, sodium dodecyl sulfate (SDS), cetylpyridinium chloride, sodium chloride, lithium chloride, potassium chloride, sodium perchlorate, lithium perchlorate, sodium iodide, and potassium iodide; aliphatic alcohols, such as butanol, ethanol, propanol and isopropanol; phenol and other phenolic compounds.

In some embodiments, to promote selective binding of high molecular weight (HMW) nucleic acids to the filter matrix, an aliphatic alcohol, such as isopropanol is provided in a range between about 0% to about 10%, preferably between about 4% to about 6% (optimal=4.7%) and a chaotropic salt, such as guanidine isothiocyanate and/or guanidine hydrochloride is provided in a range between 1.0 M to 4.0 M, preferably between about 3.0 M to about 4.0 M.

In some embodiments, to promote binding (and concentration) of low molecular weight (LMW) nucleic acids to the filter matrix, an aliphatic alcohol, such as isopropanol is provided in a range between about 10% to about 25%, preferably between about 15% to about 20% (optimal=17.7%).

In other embodiments, to promote isolation of MTB DNA from sputum, an aliphatic alcohol, such as ethanol may be provided in a range between about 20% to about 60%, preferably between about 30% to about 50% (optimal=44%)

Following the above-described inactivation and homogenization steps, the pH of the solution should be adjusted, as necessary, to achieve a pH below 7. Where the pH is above 7, the solution can be neutralized with a mild acid, such as potassium acetate or sodium phosphate. This will be necessary when using NaOH or O-phenylphenol, which have a pH>11. Low pH phenolic and hydrogen peroxide reagents are inherently acidic and will most likely not need an additional buffer.

In one embodiment, binding of nucleic acids to the filter matrix may be carried out by attaching a filter tip 124 to a syringe 176 via luer lock connections between the two. In another embodiment, the filter matrix is in the syringe 176. An exemplary filter tip 124 is shown in FIG. 4. The filter tip 124 comprises a porous silica matrix 126 embedded inside of a tip body 127, an aerosol filter 128 to prevent contamination and exposure to the user, and a tip cap 129 to help maintain a closed system. In one embodiment, the cap 129 is connected to the filter tip 124 with an insert. In some embodiments, the cap is an ordinary Falcon tube cap 208. The filter tip 124 is configured to allow a liquid sample to flow through the matrix with each aspiration and dispense cycle of the filter tip 124. Using a syringe 176 or other suitable device, the cell lysate in the container 120 is passed up through the distal end of the filter tip 124 so that nucleic acids in the cell lysate bind to the filter matrix 126 in the pipette tip 127. Typically, the cell lysate is drawn up and down through the filter matrix 126 so that the lysate and unbound portion passes through the filter matrix 126 at least two times before expelling the unbound lysate fraction out through the distal end of the pipette tip 127 into a suitable disposal receptacle 172.

Combining the sample with chaotropic reagents dehydrates the DNA and silica to promote adsorption to the porous silica matrix 126. Subsequent aspiration and dispense cycles (2-3x) of a wash buffer remove impurities from the matrix 126. At this point, filter tip 124 containing nucleic acids bound to the filter matrix 126 can be stored in a sealed container 120 for further analysis at another time. Alternatively, the bound nucleic acids can be eluted from the filter tip using a suitable elution buffer as further described below.

Figure 6:
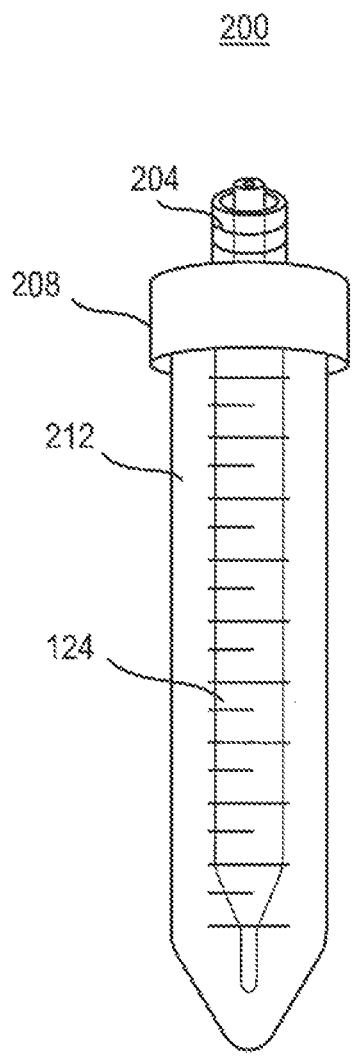
FIG. 6 depicts a disposable transport device according to another embodiment.

Nucleic acids have been shown to be very stable on solid supports, including silica, particularly when stored under dehydrated conditions without any additional stabilizers. Accordingly, in another aspect, the present application provides a means for stabilizing the purified nucleic acids for transport in the form of a single-use disposable transport device 200 comprising a luer lock adapter 204 attached to the top side of the cap 208 of a suitable holding tube 212 (e.g., 50 mL conical tube), such that the filter tip 124 attaches to the bottom side of the tube cap 208 (FIG. 6).

Before use (i.e., elution of the nucleic acids for analysis), the filter tip 124 attached to the cap 208 is removed from the holding tube 212 and attached to a syringe 176 as shown in FIG. 2. In this case, the user can readily insert and remove the filter tip 124 via the luer lock adaptor 204 while holding onto the tube cap 208, such that the holding tube 212 shields the user and the filter tip 124 from contamination. When this sequence is completed, the porous silica filter matrix 126 with bound nucleic acids can be dried and the capped filter tip 124 is screwed onto the empty holding tube 212 for transport. During transportation, the holding tube 212 protects the filter tip 124 from contamination. The stabilized nucleic acids can be rehydrated later with elution buffer and eluted off into a storage tube for long-term frozen storage or eluted directly into a detection assay device or sample tube using a similar automated system as used at the clinic or simply by using a disposable syringe 176. In the latter case, the syringe 176 can serve as the mechanism for the aspiration and dispense cycles of the elution buffer across the silica matrix 126.

In preparation for molecular analysis, aspiration and dispense cycles (2-3x) of an elution buffer remove the bound nucleic acids from the matrix 126. Completion of the process results in purified nucleic acids in a PCR-compatible buffer. This approach allows for flexibility with respect to format such that it can be used with a liquid handling system for high throughput applications or with a simple pipette tip for low throughput applications.

Figure 7:
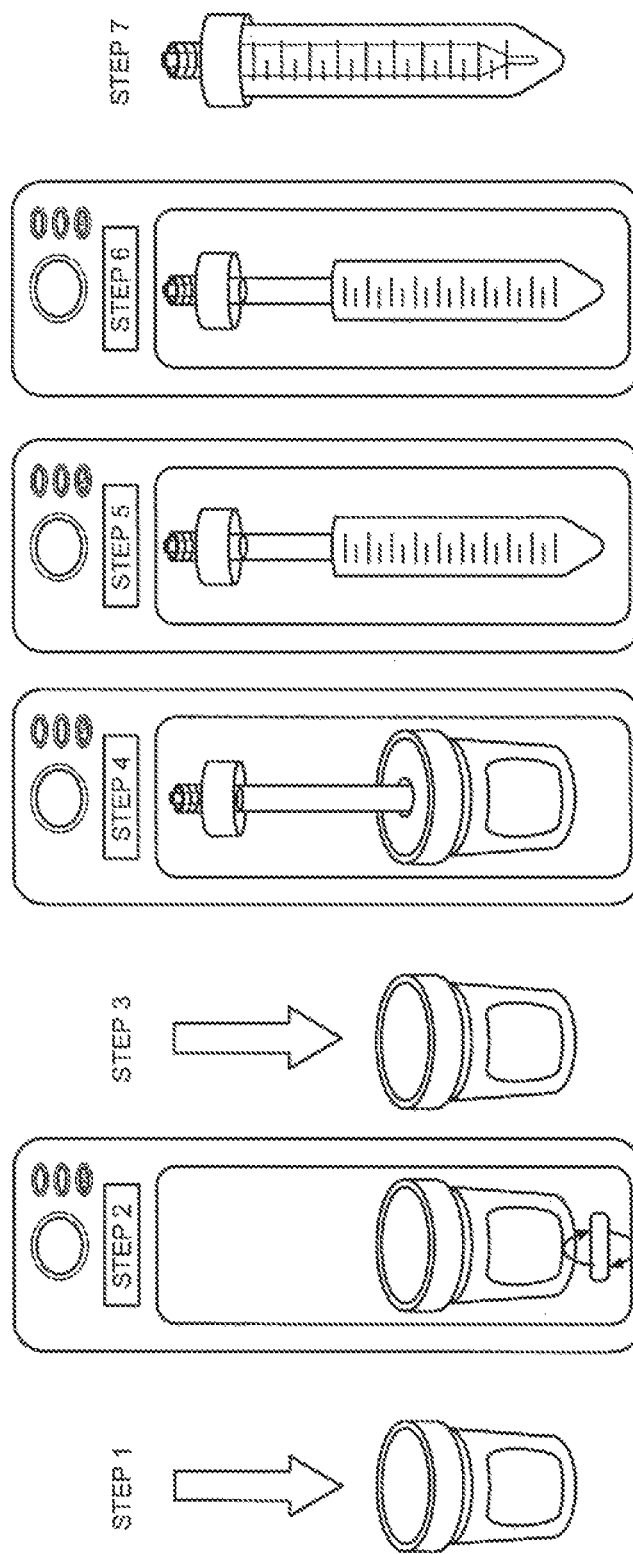
FIG. 7 illustrates an exemplary sequence of steps for MagVor/filter tip purification of nucleic acids from sputum.

FIG. 7 illustrates an exemplary sequence of steps for MagVor/filter tip purification of nucleic acids from sputum. A sputum sample suspected of containing MTB is collected with a sample container. A chemical reagent mix, including inactivating reagents and mucolytic agents are added (Step 1). The sample container is then placed on an extraction stand (or rack) and the sample contents are subjected to magnetically-induced vortexing (MagVor) for 2-15 minutes, preferably about 10 minutes (Step 2). Following lysis of the cells, the beads are allowed to settle for about 1-2 minutes and binding buffer is added to the container (Step 3). The user attaches a filter tip to the bottom side of the tube cap/luer lock adaptor in FIG. 6 and connects a syringe to the top side of the tube cap/luer lock adaptor using the luer lock connection (Step 4). The user pierces the filter tip through the cap over and into the container, and draws the cell lysate into the tip and moves the syringe lever up and down past the filter matrix 2-3 times to facilitate binding to the filter matrix, whereby the unbound portion is passed back into the tube (Step 4). Following this binding step, the sample container is replaced with a fresh tube containing wash reagent, and the filter matrix is washed with wash buffer, which is collected in the tube (Step 5). Following the wash step, the tube is raised out of the liquid. In some embodiments, the filter tip is further dried by dispensing air through the filter matrix (Step 6). In some embodiments, several rounds of air drying are performed to reduce residual wash reagent. Then the user detaches the filter tip/cap adaptor from the syringe, places the filter tip back in a fresh holding tube containing dessicant, and connects the filter tip/cap adaptor to the holding tube for storage (Step 7). The nucleic acids in the filter tip are stable for transport or can elute the purified nucleic acids from the filter tip for PCR analysis etc.

Elution of the nucleic acids may be carried out by passing elution buffer through the filter matrix 2-3 times before collection.

Additives, such as trehalose, 0.1% Triton-X-100 or DNAstable® Plus reagent (Biomatrica) may be included with the elution buffer or added to the eluted nucleic acids to enhance their stability.

In certain embodiments, the method further includes the steps of eluting the nucleic acids, amplifying the eluted nucleic acids with primers specific for a predetermined target, and determining whether the sample contains nucleic acids corresponding to the target. Preferred targets for detection include bacterial and viral pathogens found in sputum, including/but are not limited to, MTB, *Staphylococcus aureus*, methicillin resistant *Staphylococcus aureus* (MRSA), *Streptococcus pyogenes*, *Streptococcus pneumoniae*, *Streptococcus agalactiae*, *Haemophilus influenzae*, *Haemophilus parainfuluezae*, *Moraxella catarrhalis*, *Klebsiella pneumoniae*, *Escherichia coli*, *Pseudomonas aeruginosa*, *Acinetobacter* sp *Bordetella pertussis*, *Neisseria meningitidis*, *Bacillus anthracis*, *Nocardia* sp., *Actinomyces* sp., *Mycoplasma pneumoniae*, *Chlamydia pneumonia*, *Legionella species*, *Pneumocystis jiroveci*, influenza A virus, cytomegalovirus, and rhinovirus.

The system 100 described herein can detect MTB at levels of less than 1,000 cells/ml, preferably less than 100 cells/ml, more preferably less than 50 cells/ml, most preferably less than 10 cells/ml. Given that 1 colony forming unit (cfu) is roughly equivalent to 10 cells, the above system can be used to provide a detection of at least 100 cfu/ml, 10 cfu/ml, 5 cfu/ml or even 1 cfu/ml.

It should be recognized, however, that every clinical sample is unique, and will vary one to the next in viscosity, particulates, mucus, surface contaminants, microbial and/or human genetic backgrounds. Given expected variations in clinical sample composition and intended uses of an automated filter tip sample preparation protocol, it may therefore be necessary to modify certain steps in a filter tip procedure in order to achieve desired results.

For example, while the filter tips described herein have a relatively large pore size, sample homogenization and liquefaction is very important for efficient cell lysis, and subsequent binding steps to the filter matrix. With homogenous and well-liquefied lysates, samples can also be passed over the filter tip with higher flow rates, which reduces the overall sample processing time. As demonstrated with the large-volume plasma protocol below, large input sample volumes can be effectively processed with a filter tip, which provides users the opportunity to thoroughly homogenize and liquefy difficult samples (on-line or off-line), with only minor concern over input sample volumes.

Further, it should be appreciated that slower flow rates during nucleic acid binding or elution typically result in higher nucleic acid yields, albeit at the expense of total processing time. Slower flow rates will also minimize the extent of DNA shearing.

Complete drying of the filter matrix is recommended to prevent residual organic solvents from co-eluting with the purified nucleic acid sample and inhibiting downstream processes or tests. Because the filter tip is not dried via centrifugation or vacuum filtration, it is important to maximize both the flow rate and cycle numbers during the drying step.

Because the geometry, filter tip material, and attachment method to the robotic channel arms are unique for each instrument manufacturer, a different filter tip construct is required for each liquid handling system. The filter matrix dimensions (diameter, thickness, and pore size) do correlate with nucleic acid binding capacity (and elution efficiencies), as is expected for any solid-phase extraction technique. While thick (>4 mm) matrices may be embedded into a 1 ml filter tip to increase nucleic acid binding capacity for large-volume samples and/or equalize the matrix binding capacity across specific filter tip formats, there is a tradeoff between filter tip thickness and flow rates during the initial binding step (in the presence of crude lysates). Thus, it is sometimes advantageous to embed larger-diameter matrices into larger-volume filter tips for the initial steps of an automated protocol, (e.g., the 5 ml Hamilton/Akonni TruTips® for large-volume extractions). Given the specific filter tip configurations dictated by the manufacturers of liquid handling robots, however, it is not reasonable to expect the filter tip nucleic acid yields to be identical across liquid handling platforms from different manufacturers, or across different filter tip sizes. Clinical evaluation of automated filter tip protocols and direct comparisons against commercially-available automated systems will be reported in detail elsewhere.

The MagVor/filter tip process has a number of advantages compared with conventional methods. First, the process is compatible with automation. Secondly, confinement of the filter matrix within the pipette tip reduces its susceptibility to cross-contamination. Fibrous silica matrices on spin disks, on the other hand, can easily rupture and release fine particles that can be a source of contamination. Similarly, techniques that rely on the mobility of magnetic beads for purification introduces a similar risk. The relatively large porosity of the filter matrix allows high viscosity samples to flow through the matrix without clogging. The multiple aspiration and dispense cycles allow for increased binding of target nucleic acid when compared with centrifugation methods employing single passage of samples through a matrix. Moreover, the chaotropic chemistry provides an established method for removing inhibitors and nucleases, and lends itself to long-term stability.

The present invention is further illustrated by the following examples which should not be construed as limiting. The contents of all references, patents and published patent applications cited throughout this application, as well as the Figures and Tables are incorporated herein by reference.

EXAMPLES

Example 1: MagVor Homogenization and Lysis

The efficacy of the MagVor system was tested against *Bacillus thuringiensis* spores, *Streptococcus pyogenes*, and MTB in raw sputum, using a 1:1 v:v ratio of glass beads to sample volume, 1 mL total sample volume, and 30 to 120 sec of MagVor lysis. MTB DNA extraction from raw sputum is particularly challenging in view of its mycobacterial cell wall and low (10 bacilli) infectious dose. Lysis efficacy was estimated by quantitative, real-time PCR of equivalent raw sputum samples before and after MagVor treatment. MagVor processing was found to improve nucleic acid detection by an average of 2.5 cycles (nearly 1 log) relative to untreated samples (i.e., aliquots of the same sputum sample but not processed by the MagVor system).

To investigate the extent to which physical lysis kit components (particles, stir disk, coatings) may interfere with nucleic acid extraction and purification, and analysis of four bead types and three magnetic disks was undertaken to identify a lysis bead and magnetic disk that did not generate ultra-fine particulates in solution after MagVor lysis. NPA samples were pooled, confirmed negative for target DNA of interest by real-time PCR, and then spiked with intact methicillin MRSA or MTB target cells. Specimens (0.5 mL) were processed in duplicate and lysed with a 10 min MagVor treatment at 5000 rpm. The nucleic acids were purified with a manual MagVor/filter tip procedure employing a guanidinium-based binding buffer and then analyzed by quantitative, real-time PCR (or RT-PCR). Glass beads readily settled to the bottom of the lysis tubes and showed no obvious inhibition or degradation of DNA or RNA during these tests.

As shown in Table 1, a consistent improvement in DNA recovery was obtained with MagVor treatment compared to no treatment, especially at higher titers.

TABLE 1

Combined MagVor/filter tip recovery of MRSA and MTB DNA from spiked NPAs

| Organism | Titer (cfu mL$^{-1}$) | MagVor Ave. $C_1$ | No Treatment Ave. $C_1$ | $\Delta C_1$ |
|---|---|---|---|---|
| MRSA | $10^8$ | 23.69 | 28.86 | 5.17 |
|  | $10^7$ | 25.50 | 28.56 | 3.06 |
|  | $10^6$ | 29.32 | 31.67 | 2.36 |
|  | $10^5$ | 31.81 | 33.98 | 2.17 |
| MTB H37Ra | $10^7$ | 17.31 | 20.38 | 3.08 |
|  | $10^6$ | 21.33 | 23.82 | 2.49 |
|  | $10^5$ | 24.33 | 26.50 | 2.17 |
|  | $10^4$ | 28.79 | 29.77 | 0.98 |
|  | $10^3$ | 31.59 | 32.76 | 1.17 |
|  | $10^2$ | 33.63 | 34.52 | 0.89 |

Example 3: Comparison of Integrated MagVor/Filter Tip Prototype to Qiagen Nucleic Acid Purification Kits The nucleic acid lysis and purification efficacy of the integrated system was evaluated in comparison to comparable Qiagen nucleic acid purification kits. Model sample types included MRSA in NPA, influenza A in NPS, human genomic DNA from whole blood, and MTB in NPA. The Qiagen kits included the DNA Mini Kit (no mechanical lysis, but with 10 min proteinase K treatment), Viral RNA Mini Kit (no mechanical lysis, but with RNA carrier), and Mini Blood Kit (10 min proteinase K incubation). Since Qiagen does not have a specific kit for MTB extractions, a BD GeneOhm lysis kit was employed in conjunction with a Qiagen Mini DNA extraction kit. BD lysis and Qiagen kits also have a limited input sample volume, so NPA and NPS samples were processed in 200 μL volumes, and whole blood was processed in 100, 10, and 1 μL volumes. Replicate reagent plates were prepared, sealed, and processed for each sample type and titer (n=24 extractions per sample), purified nucleic acid analyzed by quantitative, real-time PCR, and average cycle-threshold (Ct) values compared to those obtained from comparable Qiagen extractions (n=8 extractions per sample). Positive and negative controls were run with each plate to test for potential cross-contamination.

The results from this analysis are summarized in Table 2, and demonstrate comparable performance and efficacy relative to the Qiagen kits. Limits of detection for MRSA in NPA and influenza A in NPS were approximately $10^3$ cells or virions/ml for both systems. Human DNA was readily recovered from 1 μL of whole blood, and no template controls showed no evidence of nucleic acid cross-contamination. These data demonstrate the extensibility and efficacy of the integrated sample preparation prototype relative to commercially-available, high-quality sample preparation kits.

TABLE 2

Nucleic acid recovery from MagVor-filter tip system (n = 24) relative to other DNA extraction kit

| Titer (cfu mL$^{-1}$, or μL) | Integrated Prototype (Ave C$_1$) | StDev | Qiagen (Ave C$_1$) | StDev |
|---|---|---|---|---|
| MRSA in NPA | 10$^6$ | 29.07 | 0.49 | 30.73 | 0.12 |
| | 10$^5$ | 33.82 | 0.87 | 33.69 | 0.26 |
| | 10$^4$ | 35.74 | 0.62 | 36.33 | 0.68 |
| | *10$^3$ | 38.82 | 0.77 | 38.86 | 1.08 |
| | NTC | Not Detected | | | |
| Influenza A In NPS | 10$^6$ | 23.47 | 0.30 | 24.91 | 0.43 |
| | 10$^5$ | 27.71 | .040 | 29.45 | 0.61 |
| | 10$^4$ | 34.02 | 0.80 | 34.61 | 0.74 |
| | *10$^3$ | 37.94 | 1.14 | 38.44 | 0.81 |
| | NTC | Not Detected | | | |
| Human DNA in Whole Blood | 100 μL | 26.87 | 0.59 | 26.26 | 0.21 |
| | 10 μL | 29.66 | 0.21 | 29.35 | 0.13 |
| | 1 μL | 32.14 | 0.37 | 32.75 | 0.47 |
| | NTC | Not Detected | | | |
| MTB in NPA | 10$^6$ | 21.20 | 0.27 | 22.04 | 0.38 |
| | 10$^5$ | 25.74 | 0.34 | 27.78 | 1.91 |
| | 10$^4$ | 28.81 | 0.46 | 30.67 | 0.67 |
| | 10$^3$ | 31.31 | 0.72 | 32.82 | 0.35 |
| | 10$^2$ | 34.35 | 0.58 | 35.67 | 0.32 |
| | NTC | Not Detected | | | |

Example 4: Sputum Liquefaction

Since most specimens submitted for mycobacterial culture are contaminated with a variety of organisms that can rapidly outgrow the mycobacteria, before analysis, respiratory specimens are typically submitted to digestion-decontamination pretreatment. Thus, mycobacteria are recovered optimally from clinical specimens through use of procedures that reduce or eliminate contaminating bacteria while releasing mycobacteria trapped in mucin and cells.

NALC-NaOH sedimentation has become the standard for decontaminating and digesting sputa specimens of non-tuberculous mycobacteria (NTMs). However, the extraction of MTB DNA from raw sputum is particularly challenging because of the high viscosity and heterogeneity of sputum, on the on hand, an the difficult-to-disrupt cell walls of MTB, on the other hand. Transport of DNA extracts reduces the logistical complexity (in terms of cold transport) compared to raw sputum. While NALC-NaOH is indeed a digestion procedure, NALC rapidly loses its activity, requiring fresh reagents to be reconstituted daily. In addition, the procedure requires centrifugation, which adds further complexity and equipment. Furthermore, NaOH exposure causes MTB cell death and degrades DNA.

Accordingly, it was of interest to develop a liquefaction method that could serve as an alternative for users who have interest in processing raw sputum. Since raw sputum is a difficult specimen type to transfer to sample containers, a single-step sputum liquefaction procedure was developed using an enzyme solution. By adding 1 part liquid enzyme to 10 parts raw sputum and incubating for 15-20 min at 56° C. even highly heterogeneous and viscous sputum specimens were liquefied to a viscosity comparable with 5-10% glycerol. These liquefied sputum specimens were readily pipetted and processed with a manual MagVor and filter tip protocol without causing the magnetic disk in the lysis tube to stop rotating or clogging the filter tip.

Example 5: Extraction of MTB DNA from Raw Sputum

An automated 8-channel prototype system depicted in FIGS. 5A and 5B was used to demonstrate the feasibility of DNA extraction from raw, TB-positive sputum. Using a Truant TB Fluorescent Stain, de-identified patient specimens were determined by smear microscopy to be either Smear 2+ or 4+. Four aliquots of Smear 2+ raw sputum specimens and four aliquots of Smear 4+ raw sputum specimens were processed according to the liquefaction protocol in Example 4 and then added to the MagVor tubes. The Integrated MagVor/filter tip protocol was then performed by automated extraction/purification. The eluent was analyzed with a IS6110 qPCR assay, and the concentrations of the extracts were found to be 3.6±0.7 pg/μL for the Smear 2+ and 49±8 pg/μL for the Smear 4+. This data supports the feasibility of the automated nucleic acid isolation instrument for extracting DNA from TB positive specimens.

Table 3 shows the results of a dilution series study comparing real-time detection of MTB using an automated vs. manual MagVor/filter tip system. MTB cells were spiked into 500 μl of TB-negative sputum and sediment (NALC-NaOH processed sputa), where 10 cells is roughly equivalent to 1 cfu/ml. Corresponding cell levels corresponding to acid-fast bacilli (AFB) smear positive and AFB smear negative are included for comparative purposes.

TABLE 3

3 Dilution series study showing real-time detection of MTB DNA by manual and automated MagVor/filter tip systems

| | Cells mL$^{-1}$ | Average C$_1$ ± StDev (n = 6 extractions, two replicate PCR$_{\text{per extraction}}$) | | |
|---|---|---|---|---|
| | | Raw Sputum | NALC-NaOH Sediment | |
| Automated TruTip | 10$^6$ | 21.24 ± 0.20 | 21.61 ± 0.12 | AFB Smear+ |
| | 10$^5$ | 26.24 ± 0.14 | 25.45 ± 0.41 | |
| | 10$^4$ | 29.05 ± 0.17 | 29.12 ± 0.32 | |
| | 10$^3$ | 31.71 ± 0.39 | 29.85 ± 0.19 | AFB Smear− |
| | 10$^2$ | 31.77 ± 0.38 | 31.19 ± 0.20 | |
| | 10$^1$ | Inconsistent | Inconsistent | |
| | 0 | ND | ND | |
| Manual TruTip | 10$^6$ | 24.98 ± 0.67 | 24.01 ± 0.40 | AFB Smear+ |
| | 10$^5$ | 26.15 ± 0.54 | 26.78 ± 0.41 | |
| | 10$^4$ | 28.18 ± 0.56 | 28.18 ± 0.43 | |
| | 10$^3$ | 30.90 ± 0.24 | 32.14 ± 0.12 | AFB Smear− |
| | 10$^2$ | 34.07 ± 0.53 | 33.24 ± 0.41 | |
| | 10$^1$ | Inconsistent | Inconsistent | |
| | 0 | ND | ND | |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for purifying molecules of interest from a sample with a sample purification system that comprises:
   a housing;
   an electric motor disposed in the housing; a sample container rack disposed in the housing, wherein the sample container rack is configured to hold one or more sample containers,
   a filter device holder disposed in the housing, wherein the filter holder is configured to hold one or more filter devices, wherein each of the filter devices comprises a filter matrix for binding molecules of interest; and
   a cylindrical magnet adjacent to the side of the sample container rack and external to the sample container rack, wherein
   the magnet rotates around a central, longitudinal axis of the magnet by an electric motor disposed in the housing and is located above the bottom of the sample container rack,
   wherein the method comprises following steps
   placing a sample container containing a liquid sample suspension, a magnetic stirrer and cell lysis beads on the sample container rack;
   homogenizing the liquid sample suspension in the sample container by rotating the cylindrical magnet at a speed such that cells in the sample suspension in the sample container are lysed by the magnetic stirrer and cell lysis beads;
   flowing the homogenized liquid sample suspension through the filter matrix of a filter device from the one or more filter devices under conditions such that the molecules of interest bind to the filter matrix, wherein the filter device is mounted on the filter device holder;
   washing the filters matrix of the filter device and eluting the molecules of interest bound to the filter matrix from the filter device, thereby purifying the molecules of interest from the sample.

2. The method of claim 1, wherein the sample container is pre-packed with one or more items selected from the group consisting of the magnetic stirrers, the cell lysis beads, reagents that facilitate cell lysis and reagents that preserve the integrity of the molecules of interest.

3. The method of claim 1, wherein the molecules of interest are nucleic acids.

4. The method of claim 3, wherein the liquid sample suspension comprises sputum.

5. The method of claim 4, wherein the molecules of interest are nucleic acids and further comprising the step of amplifying the molecules of interest eluted from the filter device with primers specific for *Mycobacterium tuberculosis* and determining whether the molecules of interest comprise *Mycobacterium tuberculosis* DNA.

6. The method of claim 1, wherein the cylindrical magnet has two magnetic poles symmetrically disposed along the longitudinal axis of the magnet.

7. The method of claim 1, wherein the cylindrical magnet has opposing magnetic poles disposed at two opposite ends of the magnet.

8. The method of claim 1, wherein the cell lysis beads are silica beads having diameters within a range from 10 μm to 1000 μm.

9. The method of claim 1, wherein the magnetic stirrer comprises an alloy core coated with a polymer.

10. The method of claim 9, wherein the alloy core of the magnetic stirrer comprises neodymium iron boron or samarium cobalt and wherein the polymer is polytetrafluoroethylene (PTFE) car parylene.

* * * * *